United States Patent
Höfgen et al.

(10) Patent No.: US 7,161,009 B2
(45) Date of Patent: Jan. 9, 2007

(54) HYDROXYINDOLES, THEIR USE AS INHIBITORS OF PHOSPHODIESTERASE 4 AND PROCESSES FOR THEIR PREPARATION

(75) Inventors: Norbert Höfgen, Ottendorf-Okrilla (DE); Ute Egerland, Radebeul (DE); Hildegard Poppe, Dresden (DE); Degenhard Marx, Radebeul (DE); Stefan Szelényi, Schwaig (DE); Thomas Kronbach, Radebeul (DE); Emmanuel Polymeropoulos, Frankfurt (DE); Sabine Heer, Radebaul (DE)

(73) Assignee: Elbion AG, Radebeul (DE)

( * ) Notice: Subject to any disclaimer, the term of this patent is extended or adjusted under 35 U.S.C. 154(b) by 86 days.

(21) Appl. No.: 10/081,642

(22) Filed: Feb. 21, 2002

(65) Prior Publication Data

US 2002/0119971 A1   Aug. 29, 2002

(51) Int. Cl.
C07D 401/12 (2006.01)

(52) U.S. Cl. .................................................. 546/278.1
(58) Field of Classification Search ............. 546/278.1; 514/339
See application file for complete search history.

(56) References Cited

U.S. PATENT DOCUMENTS

| | | | |
|---|---|---|---|
| 2,814,625 A | 11/1957 | Speeter | |
| 2,825,734 A | 3/1958 | Speeter | |
| 2,870,162 A | 1/1959 | Speeter et al. | |
| 2,930,797 A | 3/1960 | Anthony et al. | |
| 3,028,393 A | 4/1962 | Szmuszkovicz | |
| 3,188,313 A | 6/1965 | Archer | |
| 3,196,162 A | 7/1965 | Sarett et al. | |
| 3,259,622 A | 7/1966 | Shen et al. | |
| 3,271,416 A | 9/1966 | Shen | |
| 3,342,834 A | 9/1967 | Shen | |
| 3,459,770 A | 8/1969 | Freed et al. | |
| 3,527,761 A | 9/1970 | Archibald et al. | |
| 3,578,669 A | 5/1971 | Zenith | |
| 3,642,803 A | 2/1972 | Welstead, Jr. | |
| 5,192,770 A | 3/1993 | Clark et al. | |
| 5,411,972 A * | 5/1995 | Komoto et al. | 514/330 |
| 5,464,861 A * | 11/1995 | Dobrusin et al. | 514/414 |
| 6,008,231 A * | 12/1999 | Lebaut et al. | 514/314 |

FOREIGN PATENT DOCUMENTS

| | | |
|---|---|---|
| CA | 2057181 | 6/1992 |
| CA | 2195850 | 2/1996 |
| CA | 2215013 | 3/1998 |
| EP | 0 490 263 A1 | 6/1992 |
| WO | 97/23457 | 7/1997 |
| WO | WO 97/23457 A | 7/1997 |
| WO | 98/09946 | 3/1998 |
| WO | 01/47916 A1 | 7/2001 |

OTHER PUBLICATIONS

CA 129:4586, Albaugh et al., 1998.*
CA 109: 122607, Hayahi et al., 1988.*
CA 98: 100717, 1983.*
CA 94: 65469, Hurnaus et al. 1981.*
Matsuoka et al, "Hydroxyindole" CA 101:23333 (1984).*
Rehse et al, "Affinity to 5-HT receptors", CA 108:75173.*
Allen et al, "Reflectance Spectrum and, etc" CA 66:33303 (1967).*
Itoh et al, "Synthesis, Physiochemical, etc" J. Org. Chem. 1997, 62, 5898-5907.*
Liu et al, "Regiospecific Bromination, etc" J. Org Chem. 1997, 62, 7447-7456.*
Von Angerer et al, I, "2-Phenylindoles, etc", J. Med. Chem., 1984, 27, 1439-1447.*
Von Angerer et al II, "2-(Hydroxyphenyl)indoles, etc" J. Med. Chem, 1983, 26, 113-116.*
Abstract—Synthesis and Pharmacological activity of . . . in nature, Bertaccini, et al. (1967), 22(4), 229-44.
Indole Inhibitors of Human . . . acetamides, Dillard, et al. J. Med. Chem, 1996, pp. 5119-5136.

* cited by examiner

Primary Examiner—Patricia L. Morris
(74) Attorney, Agent, or Firm—Fulbright & Jaworski L.L.P.

(57) ABSTRACT

The invention relates to new hydroxyindoles of the Formula,

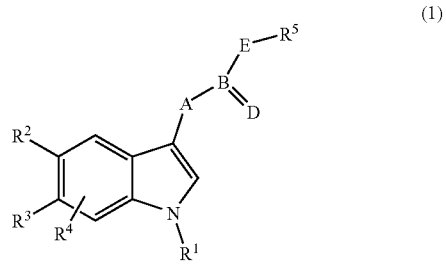

their use as inhibitors of phosphodiesterase 4 and processes for their preparation.

30 Claims, No Drawings

HYDROXYINDOLES, THEIR USE AS INHIBITORS OF PHOSPHODIESTERASE 4 AND PROCESSES FOR THEIR PREPARATION

FIELD OF THE INVENTION

The present invention relates to novel, substituted hydroxyindoles processes for their preparation, pharmaceutical preparations containing these compounds, and a method for the use of these compounds which are phosphodiesterase 4 inhibitors, as active compounds for the treatment of disorders which can be affected by inhibition of phosphodiesterase 4 activity in immunocompetent cells (e.g. macrophages and lymphocytes).

BACKGROUND

The activation of cell membrane receptors by transmitters leads to the activation of the second messenger system. Adenylate cyclase synthesizes active cyclic AMP (cAMP) or cyclic GMP (cGMP) from AMP and GMP. These lead, for example, to relaxation in smooth muscle cells or to inhibition of mediator release or synthesis in inflammatory cells. The breakdown of the second messenger cAMP and cGMP is carried out by the phosphodiesterases (PDE). To date, 7 families of PDE enzymes (PDE1-7) are known, which differ by their substrate specificity (cAMP, cGMP or both) and the dependence on other substrates (e.g. calmodulin). These isoenzymes have different functions in the body and are prominent to different extents in the individual cell types (Beave J A, Conti M and Heaslip R J, Multiple cyclic nucleotide phosphodiesterases, Mol. Pharmacol. 1994, 46: 399–405; Hall I P, Isoenzyme selective phosphodiesterase inhibitors; potential clinical uses, Br. J. clin. Pharmacol. 1993, 35: 1–7). As a result of inhibition of the various PDE isoerzyme types, there is an accumulation of cAMP or cGMP in the cells, which can be therapeutically utilized (Torphy T J, Livi G P, Christensen S B, Novel Phosphodiesterase Inhibitors for the Therapy of Asthma, Drug News and Perspectives 1993, 6: 203–214).

In the cells important for allergic inflammation (lymphocytes, mast cells, eosinophilic granulocytes, macrophages), the prevailing PDE isoenzyme is of type 4 (Torphy, J T. and Undem, B. J., Phosphodiesterase inhibitors: new opportunities for the treatment of asthma, Thorax 1991, 46: 512–523). The inhibition of PDE 4 by suitable inhibitors is therefore considered as an important starting point for the therapy of a large number of allergically induced disorders (Schudt Ch, Dent G, Rabe K, Phosphodiesterase Inhibitors, Academic Press London 1996).

An important property of phosphodiesterase 4 inhibitors is the inhibition of the release of tumour necrosis factor α (TNFα) from inflammatory cells. TNFα is an important pro-inflammatory cytokine, which affects a large number of biological processes. TNFα is released, for example, from activated macrophages, activated T lymphocytes, mast cells, basophils, fibroblasts, endothelial cells and astrocytes in the brain. It has a self-activating effect on neutrophils, eosinophils, fibroblasts and endothelial cells, as a result of which various tissue-destroying mediators are released. In monocytes, macrophages and T lymphocytes, TNFα brings about the increased production of further pro-inflammatory cytokines such as GM-CSF (granulocyte-macrophage colony-stimulating factor) or interleukin-8. TNFα plays a central part due to its inflammation-promoting and catabolic action in a large number of disorders, such as inflammation of the airways, inflammation of the joints, endotoxic shock, tissue rejection, AIDS and numerous other immunological disorders. Inhibitors of phosphodiesterase 4 are thus also suitable for the therapy of disorders of this type which are associated with TNFα.

Chronic obstructive pulmonary diseases (COPD) are widespread in the population and also have great economic importance. Thus COPD diseases cause about 10–15% of all illness costs in the developed countries and about 25% of all cases of death in the USA are to be attributed to this cause (Norman P.: COPD: New developments and therapeutic opportunities, Drug News Perspect. 11 (7), 431–437, 1998), however the patients at the time of death are usually over 55 years old (Nolte D.: Chronische Bronchitis—eine Volkskrankheit multifaktorieller Genese. Atemw.-Lungenkrkh. [Chronic bronchitis—a widespread disease of multifactorial origin]. 20 (5), 260–267, 1994). The WHO estimates that COPD will be the third most frequent cause of death within the next 20 years.

The syndrome of chronic obstructive lung diseases (COPD) summarizes various syndromes of chronic bronchitis with the symptoms coughing and expectoration and progressive and irreversible impairment of lung function (exhalation is particularly affected). The course of the disease is episodic and often complicated by bacterial infections (Rennard S. I.: COPD: Overview of definitions, Epidemiology, and factors influencing its development. Chest, 113 (4) Suppl., 235S–241S, 1998). In the course of the disease, the lung function continuously decreases, the lungs become increasingly emphysematous and the respiratory distress of the patients is obvious. This disease clearly adversely affects the quality of life of the patients (dyspnoea, low exercise tolerance) and significantly reduces their life expectancy. The main risk factor besides environmental factors is smoking (Kummer F.: Asthma und COPD. Atemw.-Lungenkrkh. 20 (5), 299–302, 1994; Rennard S. I.: COPD: Overview of definitions, Epidemiology, and factors influencing its development. Chest, 113 (4) Suppl., 235S–241S, 1998) and therefore men are clearly more often affected than women. As a result of the change in living habits and the increase in the number of smokers, this picture, however, will change in future.

The current therapy aims only at the alleviation of the symptoms, without causally intervening in the progression of the disease. The use of long-acting Beta2 agonists (e.g. salmeterol) possibly in combination with muscarinergic antagonists (e.g. ipratropium) improves the lung function by bronchodilatation and is employed routinely (Norman P.: COPD: New developments and therapeutic opportunities, Drugs News Perspect. 11 (7), 431–437, 1998). A large part in the COPD episodes is played by bacterial infections, which have to be treated with antibiotics (Wilson R.: The role of infection in COPD, Chest, 113 (4) Suppl., 242S–248S, 1998; Grossman R. F.: The value of antibiotics and the outcomes of antibiotic therapy in exacerbations of COPD. Chest, 113 (4) Suppl., 249S–255S, 1998). The therapy of this disease is unsatisfactory as yet, particularly with respect to the continuous decrease in lung function. New therapeutic approaches which affect inflammatory mediators, proteases or adhesion molecules could be very promising (Barnes P. J.: Chronic obstructive disease: new opportunities for drug development, TiPS 10 (19), 415–423, 1998).

Independently of the bacterial infections complicating the disease, a chronic inflammation which is dominated by neutrophilic granulocytes is found in the bronchi. The mediators and enzymes released by neutrophilic granulocytes, inter alia, have been held responsible for the structural changes observed in the airways (emphysema). The inhibition of the activity of the neutrophilic granulocytes is thus a rational approach to prevent or to slow down progression of COPD (impairment of lung function parameters). An important stimulus for the activation of the granulocytes is the pro-inflammatory cytokine TNFα (tumour necrosis factor). Thus it is known that TNFα stimulates the formation of oxygen radicals by neutrophilic granulocytes (Jersmann, H. P. A.; Rathjen, D. A. and Ferrante A.: Enhancement of LPS-induced neutrophil oxygen radical production by TNFα, Infection and Immunity, 4, 1744–1747, 1998). PDE4 inhibitors can very effectively inhibit the release of TNFα from a large number of cells and thus suppress the activity of the neutrophilic granulocytes. The non-specific PDE inhibitor pentoxifylline is able to inhibit both the formation of oxygen radicals and the phagocytosability of neutrophilic granulocytes (Wenisch, C.; Zedtwitz-Liebenstein, K.; Parschalk, B. and Graninger W.: Effect of pentoxifylline in vitro on neutrophil reactive oxygen production and phagocytic ability assessed by flow cytometry, Clin. Drug. Invest., 13(2):99–104, 1997).

Various PDE 4 inhibitors are already known. As a matter of priority, these are xanthine derivatives, rolipram analogues or nitraquazone derivatives (general survey in: Karlsson J-A, Aldos D, Phosphodiesterase 4 inhibitors for the treatment of asthma, Exp. Opin. Ther. Patents 1997, 7: 989–1003). Until now, it was not possible to use any of these compounds clinically. It had to be established that the known PDE 4 inhibitors also have various side-effects such as nausea and emesis, which it was not possible to suppress adequately until now. The discovery of new PDE 4 inhibitors with better therapeutic breadth is therefore necessary.

Although indoles have been playing an important part for many years in the development of new active compounds for various indications, until now hydroxyindoles were completely unknown as inhibitors of PDE 4.

DESCRIPTION OF THE INVENTION

The invention relates to substituted hydroxyindoles of the Formula

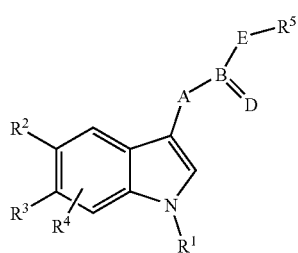

(1)

and their pharmaceutically acceptable salts, wherein
$R^1$, $R^5$ are independently of each other (i) a $C_{1-12}$ alkyl, straight chain or branched-chain, optionally mono- or polysubstituted by —OH, —SH, —NH$_2$, —NHC$_{1-6}$ alkyl, —N(C$_{16}$ alkyl)$_2$, —NHC$_{6-14}$ aryl, -N(C$_{6-14}$ aryl)$_2$, —N(C$_{1-6}$ alkyl) (C$_{6-14}$ aryl), —NHCOR$^6$, —NO$_2$, —CN, —F, —Cl, Br, —I, —O—C$_{1-6}$ alkyl, —O—C$_{6-14}$ aryl, —O(CO)R$^6$, —S—C$^{1-6}$ alkyl, —S—C$^{6-14}$ aryl, —SOR$^6$, —SO$_3$H, —SO$_2$R$^6$, —OSO$_2$C$_{1-6}$ alkyl, —OSO$_2$C$_{6-14}$ aryl, —(CS)R$^6$, —COOH, —(CO)R$^6$, mono-, bi- or tricyclic saturated or mono- or polyunsaturated car-bocycles having from 3 to 14 ring members, mono-, bi- or tricyclic saturated or mono- or polyunsaturated heterocycles having from 5 to 15 ring members and from 1 to 6 hetero atoms, which are suitable N, O and S, where the C$_{6-4}$ aryl groups and the included carbocyclic and heterocyclic substituents can optionally be mono- or polysubstituted by R$^4$.

(ii) —C$_{2-12}$ alkenyl, mono- or polyunsaturated, straight-chain or branched-chain, optionally mono- or polysubstituted by —OH, —SH, —NH$_2$, —NHC$_{1-6}$ alkyl, —N(C$_{1-6}$ alkyl)$_2$, —NHC$_{6-14}$ aryl, —N(C$_{6-14}$ aryl)$_2$, —N(C$_{1-6}$ alkyl) (C$_{6-14}$ aryl), —NHCOR$^6$, —NO$_2$, —CN, —F, —Cl, —Br, —I, —O—C$_{1-6}$ alkyl, —O—C$_{6-14}$ aryl, —O(CO)R$^6$, —S—C$_{1-6}$ alkyl, —S—C$_{6-14}$ aryl, —SOR$^6$,—SO3H, —SO$_2$R$^6$, —OSO$_2$C$_{1-6}$ alkyl, —OSO$_2$C$_{6-14}$ aryl, —(CS)R$^6$, —COOH, —(CO)R$^6$, mono-, bi- or tricyclic saturated or mono- or polyunsaturated carbocycles having from 3 to 14 ring members, mono-, bi- or tricyclic saturated or mono- or polyunsaturated heterocycles having from 5 to 15 ring members and from 1 to 6 heteroatoms, which are suitably N, O and S, where the C$_{6-14}$ a aryl groups and the included carbocyclic and heterocyclic substituents for their part can optionally be mono- or polysubstituted by R$^4$, (iii) mono-, bi- or tricyclic saturated or mono- or polyunsaturated carbocycles having from 3 to 14 ring members, optionally mono- or polysubstituted by —OH, —SH, —NH$_2$, —NHC$_{1-6}$ alkyl, —N(C$_{1-6}$ alkyl)$_2$, —NHC$_{6-14}$ aryl, —N(C$_{6-14}$ aryl)$_2$, —N(C$_{1-6}$ alkyl)(C$_{6-14}$ aryl), —NHCOR$^6$, —NO$_2$, —CN, —F, —Cl, —Br, —I, —O—C$_{1-6}$ alkyl, —O—C$_{6-14}$ aryl, —O(CO)R$^6$, —S—C$_{1-6}$ alkyl, —S—C$_{6-14}$ aryl, —SOR$^6$, —SO$_3$H, —SO$_2$R$^6$, —OSO$_2$C$_{1-6}$ alkyl, —OSO$_2$C$_{6-14}$ aryl, —(CS)R$^6$, —COOH, ——(CO)R$^6$, mono-, bi- or tricyclic saturated or mono- or polyunsaturated carbocycles having from 3 to 14 ring members, mono-, bi- or tricyclic saturated or mono- or polyunsaturated heterocycles having from 5 to 15 ring members and from 1 to 6 heteroatoms, which are suitably N, O and S, where the C$_{6-14}$ aryl groups and the included carbocyclic and heterocyclic substituents can optionally be mono- or polysubstituted by R$^4$, (iv) mono-, bi- or tricyclic saturated or mono- or polyunsaturated heterocycles having from 5 to 15 ring members and from 1 to 6 heteroatoms, which are suitably N, O and S, optionally mono- or polysubstituted by —OH, —SH, —NH$_2$, —NHC$_{1-6}$ alkyl, —N(C$_{1-6}$ alkyl)$_2$, —NHC$_{6-14}$ aryl, —N(C$_{6-14}$ aryl)$_2$, —N(C$_{1-6}$ alkyl)(C$_{6-14}$ aryl), —NHCOR$^6$, —NO$_2$, —CN, —F, —Cl, —Br, —I, —O—C$_{1-6}$ alkyl, —O—C$_{6-14}$ aryl, —O(CO)R$^6$, —S—C$_{1-6}$ alkyl, —S—C$_{6-14}$ aryl, —SOR$^6$, —SO$_3$H, —SO$_2$R$^6$, —OSO$_2$C$_{1-6}$ alkyl, —OSO$_2$C$_{6-14}$ aryl, —(CS)R$^6$, —COOH, —(CO)R$^6$, mono-, bi- or tricyclic saturated or mono- or polyunsaturated carbocycles having from 3 to 14 ring members, mono-, bi- or tricyclic saturated or mono- or polyunsaturated heterocycles having from 5 to 15 ring members and from 1 to 6 heteroatoms, which are suitably N, O and S, where the C$_{6-14}$ aryl groups and the included carbocyclic and heterocyclic substituents for their part can be optionally mono- or polysubstituted by R$^4$, -carbo- or heterocyclic saturated or mono- or polyunsaturated spirocycles having from 3 to 10 ring members, where heterocyclic systems contains from 1 to 6 heteroatoms, which are suitably N, O and S, optionally mono- or polysubstituted by —OH, —SH, —NH$_2$, —NHC$_{1-6}$ alkyl, —N(C$_{1-6}$ alkyl)$_2$, —NHC$_{6-14}$ aryl, —N(C$_{6-14}$ aryl)$_2$, —N(C$_{1-6}$ alkyl)(C$_{6-14}$ aryl), —NHCOR$^6$, —NO$_2$, —CN, —F, —Cl, —Br, —I, —O—C$_{1-6}$ alkyl, —O—C$_{6-14}$ aryl, —O(CO)R$^6$, —S—C$_{1-6}$ alkyl, —S—C$_{6-14}$ aryl, —SOR$^6$, —SO3H, —SO$_2$R$^6$, —OSO$_2$C$_{1-6}$ alkyl, —OSO$_2$C$_{6-14}$ aryl, —(CS)R$^6$, —COOH, —(CO)R$^6$, mono-, bi- or tricyclic saturated or mono- or polyunsaturated carbocycles having from 3 to 14 ring members, mono-, bi- or tricyclic saturated or mono- or polyunsaturated heterocycles having from 5 to 15 ring members and from 1 to 6 heteroatoms, which are suitably N, O and S. where the $C_{6-14}$ aryl groups and the included carbocyclic and heterocyclic substituents can optionally be mono- or polysubstituted by $R^4$, $R^2$, $R^3$ are hydrogen or —OH, where at least one of the two substituents must be —OH;

$R^4$ is —H, —OH, —SH, —NH$_2$, —NHC$_{1-6}$ alkyl, —N(C$_{1-6}$ alkyl)$_2$, —NHC$_{6-14}$ aryl, —N(C$_{6-14}$ aryl)$_2$, —N(C$_{1-6}$ alkyl)(C$_{6-14}$ aryl), —NHCOR$^6$, —NO$_2$, —CN, —COOH, —(CO)R$^6$, —(CS)R$^6$, —F, —Cl, —Br, —I, —O—C$_{1-6}$ alkyl, —O—C$_{6-14}$ aryl, —O(CO)R$^6$, —S—C$_{1-6}$ alkyl, —S—C$_{6-14}$ aryl, —SOR$^6$, —SO$_2$R$^6$.

$R^6$ is —H, —NH$_2$, —NHC$_{1-6}$ alkyl, —N(C$_{1-6}$ alkyl)$_2$, —NHC$_{6-14}$ aryl, —N(C$_{6-14}$ aryl)$_2$, —N(C$_{1-6}$ alkyl)(C$_{6-14}$ aryl), —O—C$_{1-6}$ alkyl, —O—C$_{6-14}$ aryl, —S—C$_{1-6}$ alkyl, —S—C$_{6-14}$ aryl, —C$_{1-12}$ alkyl, straight-chain or branched-chain, —C$_{2-12}$ alkenyl, mono- or polyunsaturated, straight-chain or branched-chain, -mono-, bi- or tricyclic saturated or mono- or polyunsaturated carbocycles having from 3 to 14 ring members, -mono-, bi- or tricyclic saturated or mono- or polyunsaturated heterocycles having from 5 to 15 ring members and from 1 to 6 heteroatoms, which are suitably N, O and S;

A is either a bond, or —CH2)$_m$—, —(CH2)$_m$—(CH═CH)$_n$—(CH$_2$)$_p$—, —(CHOZ)$_m$—, —(C═O)—, —(C═S)—, —(C═N—Z)—, —O—, —S—, —NZ—, where m and p are cardinal numbers from 0 to 3 and n is a cardinal number from 0 to 2, Z is H, or a $C_{1-12}$ alkyl, straight-chain or branched-chain, $C_{2-12}$ alkenyl, mono- or polyunsaturated, straight-chain or branched-chain, mono-, bi- or tricyclic saturated or mono- or polyunsaturated carbocycles having from 3 to 14 ring members, mono-, bi- or tricyclic saturated or mono- or polyunsaturated heterocycles having from 5 to 15 ring members and from 1 to 6 heteroatoms, which are suitably N, O and S;

B is either carbon or sulfur, or —(S═O)—;

D is oxygen, sulfur, CH$_2$ or N—Z, where D can only be S or CH$_2$ if B is carbon;

E is a bond, or (CH2)$_m$—, —O—, —S—, —(N—Z)—, where m and Z have the same meanings as above.

The most suitable compounds of Formula (1) include

N—(3,5-dichloropyridin-4-yl)-2-[1-(4-fluorobenzyl)-5-hydroxyindol-3-yl]-2-oxoacetamide;

N-(3,5-dichloropyridin-4-yl)-2-[1-(4-fluorobenzyl)-5-hydroxyindol-3-yl]-2-oxoacetamide Na salt;

N-(3,5-dichloropyridin-4-yl)-2-[1-(4-fluorobenzyl)-5-hydroxyindol-3-yl]-2-hydroxyacetamide;

N-(pyridin-4-yl)-2-[1-2,6-difluorobenzyl)-5-hydroxyindol-3-yl]-2-oxoacetamide;

N-(3,5-dichloropyridin-4-yl)-2-[1-(2,6-difluorobenzyl)-5-hydroxyindol-3-yl]-2-oxoacetamide;

N-(3,5-dichloropyridin-4-yl)-2-[1-(3-nitrobenzyl)-5-hydroxyindol-3-yl]-2-oxoacetamide Na salt;

N-(3,5-dichloropyridin-4-yl)-2-(1-propyl-5-hydroxyindol-3-yl)-2-oxoacetamide;

N-(3,5-dichloropyridin-4-yl)-2-(1-isopropyl-5-hydroxyindol-3-yl)-2-oxoacetamide;

N-(3,5-dichloropyridin-4-yl)-2-(1-cyclopentylmethyl-5-hydroxyindol-3-yl)-2-oxoacetamide;

N-(2,6-dichlorophenyl)-2-[1-(4-fluorobenzyl)-5-hydroxyindol-3-yl]-2-oxoacetamide;

N-(2,6-dichloro-4-trifluoromethylphenyl)-2-[1-(4-fluorobenzyl)-5-hydroxyindol-3-yl]-2-oxoacetamide;

N-(2,6-dichloro-4-trifluoromethoxylphenyl)-2-[1-(4-fluorobenzyl)-5-hydroxyindol-3-yl]-2-oxoacetamide;

N-(3,5-dichloropyridin-4-yl)-2-[1-(4-fluorobenzyl)-6-hydroxyindol-3-yl]-2-oxoacetamide;

N-(3,5-dichloropyridin-4-yl)-5-hydroxy-1-(4-methoxybenzyl)indole-3-carboxamide.

The pharmaceutically acceptable salts are obtained in a customary manner by neutralization of the bases with inorganic or organic acids or by neutralization of the acids with inorganic or organic bases. Possible inorganic acids are, for example, hydrochloric acid, sulfuric acid, phosphoric acid or hydrobromic acid, organic acids are, for example, carboxylic, sulfo or sulfonic acids such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid. Possible inorganic bases are, for example, sodium hydroxide solution, potassium hydroxide solution, ammonia, and possible organic bases are amines, suitably tertiary amines, such as trimethylamine, triethylamine, pyridine, N,N-dimethylaniline, quinoline, isoquinoline, (-picoline, (-picdine, (-picoline, quinaldine or pyrimidine.

In addition, pharmaceutically acceptable salts of the compound of Formula (1) can be obtained by converting derivatives which have tertiary amino groups into the corresponding quaternary ammonium salts in a manner known per se by using quaternizing agents. Possible quaternizing agents are, for example, alkyl halides such as methyl iodide, ethyl bromide and n-propyl chloride, but also arylalkyl halides such as benzyl chloride or 2-phenylethyl bromide.

Furthermore, the invention of the compounds of Formula (1) which contain an asymmetric carbon atom relates to the D form, the L form and D,L mixtures and, in the case of a number of asymmetric carbon atoms, the diastereomeric forms. Those compounds of Formula (1) which contain asymmetric carbon atoms and as a rule are obtained as racemates can be separated into the optically active isomers in a manner known per se, for example using an optically active acid. However, it is also possible to employ an optically active starting substance from the start, a corresponding optically active or diastereomeric compound then being obtained as the final product.

The compounds of the present invention have therapeutically useful pharmacological properties as inhibitors of the release of TNFα. These disorders include, for example, arthritides including arthritis and rheumatoid arthritis and other arthritic disorders such as rheumatoid spondylitis and osteoarthritis. Further possibilities of their application include the treatment of patients suffering from sepsis, septic shock, gram-negative sepsis, toxic shock syndrome, respiratory distress syndrome, asthma and other chronic pulmonary disorders, bone resorption diseases or transplant rejection reactions or other autoimmune disorders, such as lupus erythematosus, multiple sclerosis, glomerulonephritis and uveitis, insulin-dependent diabetes mellitus and chronic demyelinization.

Moreover, the compounds of the present invention can also be employed for the therapy of infections such as virus and parasite infections, for example, for the therapy of malaria, infection-related fever, infection-related myalgia, AIDS and cachexia.

The compounds according to the invention are inhibitors of phosphodiesterase 4 (PDE 4). Therefore, the compounds of Formula (1) and their salts, and pharmaceutical preparations which contain these compounds or their salts, can be used for the treatment of disorders in which inhibition of phosphodiesterase 4 is beneficial.

Thus the compounds according to the invention can be employed as bronchodilators and for asthma prophylaxis. Compounds of Formula (1) also inhibit of the accumulation and activity of eosinophils. Accordingly, the compounds according to the invention can also be employed in disorders in which eosinophils play a part. These disorders include, for example, inflammatory airway disorders such as bronchial asthma, allergic rhinitis, allergic conjunctivitis, atopic dermatitis, eczema, allergic angiitis, inflammations mediated by eosinophils such as eosinophilic fasciitis, eosinophilic pneumonia and PIE syndrome (pulmonary infiltration with eosinophilia), urticaria, ulcerative colitis, Crohn s disease and proliferative skin disorders such as psoriasis or keratosis.

According to the present invention the compounds of Formula (1) and their salts can inhibit both the lipopolysaccharide (LPS)-induced release of TNFα in human blood in vitro, and the LPS-induced pulmonary neutrophilic infiltration in ferrets and domestic pigs in vivo. A the pharmacologically important properties that were found confirm that the compounds of Formula (1) and their salts as well as pharmaceutical preparations which contain these compounds or their salts can be used therapeutically for the treatment of chronic obstructive pulmonary diseases.

The compounds of the invention also have neuroprotective properties and can be used for the therapy of diseases in which neuroprotection is beneficial. Such disorders are, for example, senile dementia (Alzheimer's disease), loss of memory, Parkinson's disease, depression, stroke and intermittent claudication.

Further applications of the compounds of the invention include the prophylaxis and therapy of prostate diseases, such as, for example, benign prostate hyperplasia, pollakiuria, nycturia and for the treatment of atony of the bladder and of colics caused by kidney stones.

Finally, the compounds according to the invention can also be used for the inhibition of the development of drug dependence on repeated use of analgesics, such as, for example, morphine, and for the reduction of the development of tolerance on repeated use of these analgesics.

An effiective amount of the compounds according to the invention or their salts is used for producing medicaments of the present invention, along with conventional pharmaceutical auxiliaries, carriers and additives.

The dose of the active compounds can vary depending on factors such as the route of administration, age and weight of the patient, nature and severity of the disorders to be treated and similar factors. Therefore, any reference herein to a pharmacologically effective amount of the compounds of the present invention refers to the aforementioned factors.

The daily dose can be given as an individual dose to be administered once or subdivided into two or more daily doses suitably from about 0.001 mg to about 100 mg each.

Possible forms of administration include oral, parenteral, intravenous, transdermal, topical, inhalational and intranasal preparations. For administration, possible customary pharmaceutical dosage forms include tablets, coated tablets, capsules, dispersible powders, granules, aqueous solutions, aqueous or oily suspensions, syrup, juices and drops.

Solid pharmaceutical forms can contain inert ingredients and carriers, such as, for example, calcium carbonate, calcium phosphate, sodium phosphate, lactose, starch, mannitol, alginates, gelatin, guar gum, magnesium or aluminium stearates, methylcellulose, talc, highly disperse salicylic acids, silicone oil, high molecular weight fatty acids (such as stearic acid), gelatin, agar-agar or vegetable or animal fats and oils, solid high molecular weight polymers (such as polyethylene glycol); preparations suitable for oral administration can, if desired, contain additional flavorings and/or sweeteners.

Liquid pharmaceutical forms can be sterilized and/or optionally contain auxiliaries such as preservatives, stabilizers, wetting agents, penetrating agents, emulsifiers, spreading agents, solubilizers, salts, sugars or sugar alcohols for regulation of the osmotic pressure or for buffering, and/or viscosity regulators.

Additives of this type include, for example, tartrate and citrate buffers, ethanol, complexing agents (such as ethylenediaminetetraacetic acid and its nontoxic salts). For regulation of the viscosity, possible high molecular weight polymers are those such as, for example, liquid polyethylene oxide, microcrystalline celluloses, carboxymethylcelluloses, polyvinylpyrrolidones, dextrans or gelatin. Solid carriers include, for example, starch, lactose, a mannitol, methylcellulose, talc, highly disperse salicylic acids, high molecular weight fatty acids (such as stearic acid), gelatin, agar-agar, calcium phosphate, magnesium stearate, animal and vegetable fats, solid high molecular weight polymers such as polyethylene glycol.

Oily suspensions for parenteral or topical application can include vegetable synthetic or semi-synthetic oils such as, for example, liquid $C_{8-22}$ fatty acid esters, for example palmitic, lauric, tridecylic, margaric, stearic, arachidic, myristic, behenic, pentadecanoic, linoleic, elaidic, brassidic, erucic or oleic acid, which are esterified with mono- to $C_{1-6}$ trihydric alcohols, such as, for example, methanol, ethanol, propanol, butanol, pentanol or their isomers, glycol or glycerol. Fatty acid esters of this type are, for example, commercially available Miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters such as artificial duck preen gland fat, isopropyl cocoate, oleyl oleate, decyl oleate, ethyl lactate, dibutyl phthalate, diisopropyl adipate, polyol fatty acid esters and others. Also suitable are silicone oils of differing viscosities or fatty alcohols such as isotridecyl alcohol, 2-octyldodecanol, cetylstearyl alcohol or oleyl alcohol, fatty acids such as, for example, oleic acid. Furthermore, vegetable oils such as castor oil, almond oil, olive oil, sesame oil, cottonseed oil, groundnut oil or soya bean oil can be used.

Possible solvents, gel-forming agents and solubilizers are water or water-miscible solvents. Those suitable are, for example, alcohols such as, for example, ethanol or isopropyl alcohol, benzyl alcohol, 2-octyldodecanol, polyethylene glycols, phthalates, adipates, propylene glycol, glycerol, di- or tripropylene glycol, waxes, methylcellosolve, cellosolve, esters, morpholines, dioxane, dimethyl sulphoxide, dimethylformamide, tetrahydrofuran, cyclohexanone etc.

Film-forming agents which can be used are cellulose ethers which can dissolve or swell both in water and in organic solvents, such as, for example, hydroxypropylmethylcellulose, methylcellulose, ethylcellulose or soluble starches.

Mixed forms between gel- and film-forming agents are also possible. Those used here are especially ionic macromolecules, such as, for example, sodium carboxymethylcellulose, polyacrylic acid, polymethacrylic acid and its salts, sodium amylopectin semiglycolate, alginic acid or propylene glycol alginate as the sodium salt, gum arabic, xanthan gum, guar gum or carrageenan.

Further formulation auxiliaries which can be employed include glycerol, paraffin of differing viscosities, triethanolamine, collagen, allantoin, novantisolic acid.

The use of surfactants, emulsifiers or wetting agents can also be necessary for formulation, such as, for example, of Na lauryl sulfate, fatty alcohol ether sulfates, di-Na N-lauryl-(-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenyl polyglycol ethers, cetyltrimethylammonium chloride or mono-/dialkyl polyglycol ether orthophosphoric acid monoethanolamine salts.

Stabilizers such as montmorillonites or colloidal salicylic acids for the stabilization of emulsions or for the prevention of the breakdown of the active substances, such as antioxidants, for example tocopherols or butylhydroxyanisole, or preservatives, such as p-hydroxybenzoic acid esters, can likewise optionally be required for the preparation of the desired formulations.

Preparations for parenteral administration can be present in separate dose unit forms such as, for example, ampoules or vials. Suitably, solutions of the active compound are used, most suitably aqueous solutions and especially isotonic solutions, and also suspensions. These injection forms can be made available as finished preparations or prepared only directly before administration by mixing the active compound, for example the lyophilizate, if appropriate with further solid carriers, with the desired solvent or suspending agent.

Intranasal preparations can be present as aqueous or oily solutions or as aqueous or oily suspensions. They can also be present as lyophilizates, which are prepared before administration using the suitable solvent or suspending agent.

The production, dispensation and sealing of the preparations is carried out under the conventional antimicrobial and aseptic conditions.

The invention furthermore relates to processes for the preparation of the compounds according to the invention.

According to the invention, the compounds of Formula (1) are prepared by converting compounds of Formula (1), wherein $R^2$ or $R^3$ or $R^2$ and $R^3$ are —O—$R^7$, into the compounds of the invention by removal of $R^7$, wherein $R^7$ is a substituent suitable as a leaving group, such as, for example, alkyl, cycloalkyl, arylalkyl, aryl, heteroaryl, acyl, alkoxycarbonyl, aryloxycarbonyl, aminocarbonyl, N-substituted aminocarbonyl, silyl or sulfonyl groups, and complexing agents, such as, for example, compounds of boric acid, phosphoric acid and covalently or coordinatively bonded metals, such as zinc, aluminium or copper.

Particularly suitable reactions for the removal of $R^7$ are hydrolyses using suitable bases, such as, for example, sodium hydroxide solution, potassium hydroxide solution or sodium carbonate or potassium carbonate.

These hydrolyses are suitably used when $R^7$ is an acyl, alkoxycarbonyl, aryloxycarbonyl, aminocarbonyl, N-substituted aminocarbonyl, silyl or sulfonyl residue, and a complexing agent, such as, for example, compounds of boric acid, phosphoric acid and coordinatively bonded metals, such as zinc, aluminium or copper. Particularly suitable reactions for preparing the compounds of the invention for the removal of $R^7$ from the compounds in which $R^7$ is an alkyl, cycloalkyl, arylalkyl, aryl or heteroaryl residue, are ether cleavages, for example by means of hydrobromic acid, hydrochloric acid, hydriodic acid, and using activating Lewis acids, such as, for example, AlCl3, BF3, BBr₃ or LiCl, in each case optionally in the presence of additional activators, such as, for example, ethane-1,2-dithiol or benzyl mercaptan, and ether cleavages by means of hydrogen, at elevated pressure or at normal pressure, in the presence of a suitable catalyst, such as, for example, a palladium or iridium catalyst.

According to the invention, the compounds of Formula (1) can also be prepared by converting the substructure:

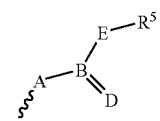

of compounds of Formula (1) by a reaction known per se into other compounds of Formula (1). Particularly suitable conversion reactions with compounds of Formula (1) are, for example, when A is —(C=O), reductions to result in A being —(CH—OH)— or A being —CH$_2$—, by reducing agents known per se, such as, for example, sodium borohydride, or by hydrogenations, which can optionally also be carried out stereoselectively.

Further suitable conversion reactions are the conversion of compounds in which D and E are oxygen into substances in which only D is oxygen, but E is —(N—Z)—, where Z has the definition given above.

Exemplary processes show below the preparation of compounds of Formula (1) according to the invention from starting substances of the type described, in which $R^7$ is an alkyl, cycloalkyl, arylalkyl, aryl or heteroaryl residue.

EXAMPLE 1

N-(3,5-Dichloropyridin-4-yl)-2-[1-(4-fluorobenzyl)-5-hydroxyindol-3-yl]-2-oxoacetamide 1.4 g of N-(3,5-dichloropyridin-4-yl)-2-[1-(4-fluorobenzyl)-5-methoxyindol-3-yl]-2-oxoacetamide (3 mmol) is dissolved in 100 ml of dichloromethane. The solution is heated to reflux and treated with a solution of 14 mmol of BBr₃ in 15 ml of dichloromethane with stirring. The reaction mixture is refluxed for 3 hours. After cooling, the solution is intensively stirred for 3 hours at 20° C. with 200 ml of an aqueous sodium hydrogencarbonate solution. The product crystallizes out, it is isolated, dried at 60° C. and recrystallized from 80 ml of ethanol.

Yield: 1.1 g (80% of theory)

Melting point: 213–214° C.

EXAMPLE 2

N-(3,5-Dichloropyridin-4-yl)-2-[1-(4-fluorobenzyl)-5-hydroxyindol-3-yl]-2-oxoacetamide 5 g (38 mmol) anhydrous aluminium chloride is introduced into 50 ml ethane-1,2,-dithiol. A solution of 4.7 g of N-(3,5-dichloropyridin-4-yl)-2-[1-(4-fluorobenzyl)-5-methoxyindol-3-yl]-2-oxoacetamide (10 mmol) in 50 ml of dichloromethane is added at 0° C. The mixture is stirred at 0° C. for 4 hours. 50 ml of 10% hydrochloric acid is added dropwise at from 0 to 10° C. with stirring. The crystallizing product is isolated, washed with water and dried at 20° C. A pure product is obtained by recrystallization from ethanol (180 ml).

Yield: 3.1 g (67% of theory)

Melting point: 212–214° C.

Exemplary preparative process as follows for compounds of Formula (1) from starting substances of the type described, in which $R^7$ is an acyl, alkoxycarbonyl, aryloxycarbonyl, aminocarbonyl, N-substituted aminocarbonyl, silyl or sulfonyl residue:

EXAMPLE 3

N-(3,5-Dichloropyridin-4-yl)-2-[1-(4-fluorobenzyl)-5-hydroxyindol-3-yl]-2-oxoacetamide Na salt 5 g of N-(3,5-dichloropyridin-4-yl)-2-[5-acetoxy-1-(4-fluorobenzyl)-indol-3-yl]-2-oxoacetamide (10 mmol) are stirred at 40° C. -50° C. for 1 hour in 50 ml dilute sodium hydroxide solution. The solution is neutralized with 10% hydrochloric acid while cooling with ice, and is concentrated to dryness. The residue is dissolved in 80 ml acetone and insoluble constituents are removed. The clear solution is treated with a solution of 0.4 g NaOH in 3 ml of water and stirred at 20° C. for 2 hours. The crystallized product is isolated, washed with acetone and dried at 60° C.

Yield: 2.44 g (51% of theory)
Melting point: 265° C.

An exemplary preparation process follows for compounds of Formula (1) from other compounds of Formula (1).

EXAMPLE 4

N-(3,5-Dichloropyridin-4-yl)-2-[1-(4-fluorobenzyl)-5-hydroxyindol-3-yl]-2-hydroxyacetamide 1 g of N-(3,5-dichloropyridin-4-yl)-2-[1-(4-fluorobenzyl)-5-hydroxyindol-3-yl]-2-oxoacetamide (1; 2 mmol) are suspended in 75 ml methanol. After addition of a solution of 0.2 g of sodium borohydride in 3 ml dilute sodium hydroxide solution, the reaction mixture is stirred at 20° C. for 6 hours. After the solvent has been removed by distillation, the residue is recrystallized from 40 ml ethanol.

Yield: 0.5 g (50% of theory)
Melting point: 205–207° C.

Numerous further compounds of Formula (1) can be prepared, as shown in the Examples and also in the further examples, all summarized in next table.

The compounds according to the invention are strong inhibitors of phosphodiesterase 4 and TNFα release. Their therapeutic potential is confirmed in vivo, for example, by the inhibition of the asthmatic late-phase reaction (eosinophilia) in guinea-pigs and by the influencing of the allergen-induced vascular permeability in actively-sensitized brown Norway rats.

The PDE 4 inhibiting activity is determined in enzyme preparations of human polymorphonuclear lymphocytes (PMNLs), the PDE 2, 3 and 5 activity with PDE from human platelets. Human blood was anticoagulated with citrate. The thrombocyte-rich plasma in the supernatant is separated from the erythrocytes and leucocytes by centrifugation at 700×g for 20 minutes at RT. The platelets are lysed by ultrasound and employed in the PDE 3 and PDE 5 assay. For the determination of the PDE 2 activity, the cytosolic platelet fraction is purified on an anion exchange column by means of NaCl gradients and the PDE 2 peak is recovered for the assay. The PMNLs for the PDE 4 determination are isolated by a following dextran sedimentation and subsequent gradient centrifugation using Ficoll-Paque. After a second washing of the cells, the erythrocytes still contained are lysed in the course of 6 minutes at 4° C. by the addition of 10 ml of hypotonic buffer (155 mM $NH_4Cl$, 10 mM $NaHCO_3$, 0.1 mM EDTA, pH 7.4). The still intact PMNLs are washed with PBS a further two times and lysed by means of ultrasound. The supernatant of a one-hour centrifugation at 4° C. at 48,000×g contains the cytosolic fraction of the PDE 4 and is employed for the PDE 4 measurements.

The phosphodiesterase activity is determined with some modifications according to the method described by Thompson et al. (Thompson, W. J.; Appleman, M. M., Assay of cyclic nucleotide phosphodiesterase and resolution of multiple molecular forms of the enzyme, Adv. Cycl. Nucl. Res. 1979, 10, of multiple molecular forms of the enzyme, Adv. Cycl. Nucl. Res. 1979, 10, 69–92).

The reaction mixtures contain 50 mM tris HCl (pH 7.4), 5 mM $MgCl_2$, the inhibitors in variable concentrations, the corresponding enzyme preparation and also the further components necessary for the detection of the individual isoenzymes (see below). The reaction is started by the addition of the substrate 0.5 μM [$^3$H]-cAMP or [$^3$H]-cGMP (about 6000 CPM/test). The final volume is 100 ml. Test substances are

| Ex. | $R^1$ | $R^2$ | $R^3$ | $R^4$ | $R^5$ | A | B | D | E | Melting point [° C.] |
|---|---|---|---|---|---|---|---|---|---|---|
| 1 | 4-Fluorobenzyl | —OH | —H | —H | 3,5-Dichloro-4-pyridyl | —(C=O)— | C | O | —(N—H)— | 215 |
| 2 | 4-Fluorobenzyl | —O$^-$ Na$^+$ | —H | —H | 3,5-Dichloro-4-pyridyl | —(C=O)— | C | O | —(N—H)— | 265 |
| 3 | 4-Fluorobenzyl | —OH | —H | —H | 3,5-Dichloro-4-pyridyl | —(CHOH)— | C | O | —(N—H)— | 205–207 |
| 4 | 2,6-Difluorobenzyl | —OH | —H | —H | 4-Pyridyl | —(C=O)— | C | O | —(N—H)— | 327–329 |
| 5 | 2,6-Difluorobenzyl | —OH | —H | —H | 3,5-Dichloro-4-pyridyl | —(C=O)— | C | O | —(N—H)— | 266–268 |
| 6 | 3-Nitrobenzyl | —O$^-$ Na$^+$ | —H | —H | 3,5-Dichloro-4-pyridyl | —(C=O)— | C | O | —(N—H)— | 235–238 dec. |
| 7 | n-Propyl | —OH | —H | —H | 3,5-Dichloro-4-pyridyl | —(C=O)— | C | O | —(N—H)— | 280–282 |
| 8 | Isopropyl | —OH | —H | —H | 3,5-Dichloro-4-pyridyl | —(C=O)— | C | O | —(N—H)— | 245–247 |
| 9 | Cyclopentylmethyl | —OH | —H | —H | 3,5-Dichloro-4-pyridyl | —(C=O)— | C | O | —(N—H)— | 246–248 |
| 10 | 4-Fluorobenzyl | —OH | —H | —H | 2,6-Dichlorophenyl | —(C=O)— | C | O | —(N—H)— | 216–218 |
| 11 | 4-Fluorobenzyl | —OH | —H | —H | 2,6-Dichloro-4-trifluoromethylphenyl | —(C=O)— | C | O | —(N—H)— | 199–201 |
| 12 | 4-Fluorobenzyl | —OH | —H | —H | 2,6-Dichloro-4-trifluoromethoxyphenyl | —(C=O)— | C | O | —(N—H)— | 176–178 |
| 13 | 4-Fluorobenzyl | —H | —OH | —H | 3,5-Dichloro-4-pyridyl | —(C=O)— | C | O | —(N—H)— | 212–213 |
| 14 | 4-Methoxybenzyl | —OH | —H | —H | 3,5-Dichloro-4-pyridyl | — | C | O | —(N—H)— | 239–241 | prepared as stock solutions in DMSO. The DMSO concentration in the reaction mixture is 1% v/v. At this DMSO concentration, the PDE activity is not affected. After the start of the reaction by means of substrate addition, the samples are incubated at 37° C. for 30 minutes. The reaction is stopped by heating the test tubes for 2 minutes at 110° C. The samples remain in the ice for a further 10 minutes. After the addition of 30 µl of 5 -nucleotidase (1 mg/ml, of a snake venom suspension from Crotalus adamanteus) incubation is carried out for 10 minutes at 37° C. The samples are stopped on ice, 400 µl each of a mixture of Dowex-water-ethanol (1+1+1) are added, and the samples are well mixed and again incubated on ice for 15 minutes. The reaction vessels are centrifuged at 3000×g for 20 minutes. 200 µl aliquots of the supernatant are transferred directly to scintillation vessels. After the addition of 3 ml of scintillator, the samples are measured in a beta counter.

[$^3$H]-cAMP is used as a substrate for the determination of the PDE 4, 3 and 2 activity, [$^3$H]-cGMP for the determination of the PDE 5 activity. The non-specific enzyme activities in each case are determined in the presence of 100 µM rolipram in the case of PDE 4 and in the presence of 100 µM IBMX in the determination of PDE 3 and 5 and subtracted from the test values. The incubation batches of the PDE 3 assay contain 10 µM rolipram in order to inhibit possible contamination by the PDE 4. The PDE 2 is tested using an SPA assay from Amersham. The assay is carried out in the presence of the activator of PDE 2 (5 µM cGMP).

$IC_{50}$ values in the range from $10^{-9}$ to $10^{-5}$ M were calculated for the compounds according to the invention in relation to the inhibition of phosphodiesterase 4. The selectivity to the PDE types 2, 3 and 5 is factor 100 to 10,000.

For the determination of the inhibition of TNFα release from cells of nasal polyps, the experimental arrangement essentially corresponds to the method described by Campbell, A. M. and Bousquet J (Anti-allergic activity of $H_1$-blockers, Int. Arch. Allergy Immunol., 1993, 101, 308–310). The starting material is nasal polyps (obtained from operation) of patients who have been subjected to surgical treatment.

The tissue is washed with RPMI 1640 and then broken down at 37° C. for 2 hours using protease (2.0 mg/ml), collagenase (1.5 mg/ml), hyaluronidase (0.75 mg/ml) and DNAse (0.05 mg/ml) (1 g of tissue to 4 ml of RPMI 1640 with enzymes). The cells obtained, a mixture of epithelial cells, monocytes, macrophages, lymphocytes, fibroblasts and granulocytes, are filtered and washed by repeated centrifugation in nutrient solution, passively sensitized by addition of human IgE and the cell suspension is adjusted to a concentration of 2 million cells/ml in RPMI 1640 (supplemented with antibiotics, 10% foetal calf serum, 2 mM glutamine and 25 mM Hepes). This suspension is distributed in 6-well cell culture plates (1 ml/well). The cells are preincubated for 30 min with the test substances in various final concentrations and then stimulated to TNFα release by addition of anti-IgE (7.2 µg/ml). The maximum release into the nutrient medium takes place after about 18 hours. In this period, the cells are incubated at 37° C. and 5% $CO_2$. The supernatant nutrient medium is recovered by centrifugation (5 min, 4000 rpm) and stored at −70° C. until cytokine determination. The determination of TNFα in the supernatant is carried out using so-called sandwich ELISAs (basic material Pharmingen), in which concentrations of the cytokine in the range from 30–1000 pg/ml can be detected.

Cells not stimulated with anti-IgE barely produce TNFα, stimulated cells, however, secrete large amounts of TNFα, which can be decreased in a dose-dependant manner, for example, by PDE 4 inhibitors. The $IC_{50}$ (concentration at 50% inhibition) is calculated from the percentage inhibition (TNFα release of the cells stimulated with anti-IgE=100%) of the tested substances at various concentrations.

For the compounds according to the present invention, $IC_{50}$ values in the range of $10^{-7}$ to $10^{-5}$ M were determined.

The inhibition of the pulmonary eosinophil infiltration by the substances is investigated in an in vivo test of the inhibition of the late-phase eosinophilia 24 hours after inhalational ovalbumin challenge of actively sensitized guinea-pigs on male Dunkin-Hartley guinea-pigs (200–250 g) actively sensitized against ovalbumin (OVA). The sensitization is carried out by means of two intraperitoneal injections of a suspension of 20 µg of OVA together with 20 mg of aluminium hydroxide as an adjuvant in 0.5 ml of physiological saline solution per animal on two successive days. 14 days after the second injection, the animals are pretreated with mepyramine maleate (10 mg/kg i.p.) in order to protect them from anaphylactic death. 30 minutes later, the animals are exposed for 30 sec in a plastic box to an OVA aerosol (0.5 mg/ml) which is generated by a nebulizer driven with compressed air (19.6 kPa) (allergen challenge). Control animals are nebulized with physiological saline solution. 24 hours after the challenge, the animals are anaesthetized with an overdose of ethylurethane (1.5 g/kg of body weight i.p.) and a bronchoalveolar lavage (BAL) is carried out using 2×5 ml of physiological saline solution. The BAL fluid is collected, centrifuged at 300 rpm for 10 min and the cell pellet is then resuspended in 1 ml of physiological saline solution. The eosinophils in the BAL are counted using an automatic cell differentiation apparatus (Bayer Diagnostics Technicon H1). 2 control groups (nebulization with physiological saline solution and nebulization with OVA solution) are included in each test.

The percentage inhibition of eosinophilia of the test group treated with substance is calculated according to the formula:

$$\% \text{ inhibition} = 100 - \frac{100 \times (B - C)}{(A - C)}$$

wherein
A is eosinophils in the control group with OVA challenge and vehicle
B is eosinophils in the group with OVA challenge treated with substance
C is eosinophils in the control group with 0.9% strength NaCl challenge and vehicle The test substances are administered intraperitoneally or orally as a suspension in 10% polyethylene glycol 300 and 0.5% strength 5-hydroxy-ethylcellulose 2 hours before the allergen challenge. The control groups are treated with the vehicle according to the form of administration of the test substance.

The compounds according to the invention were found to inhibit late-phase eosinophilia by 30% to 80% after intraperitoneal administration of 10 mg/kg and by 40% to 70% after oral administration of 30 mg/kg. The compounds according to the invention are thus particularly suitable for the production of drugs for the treatment of disorders which are connected with the action of eosinophils.

The effect of allergen-induced vascular permeability was determined on actively sensitized male brown Norway rats. Male brown Norway rats weighing 280–300 g are actively sensitized on 2 successive days by intraperitoneal injection of a suspension of 1 mg of ovalbumin together with 100 mg of aluminium hydroxide in 1 ml/animal. Three weeks after sensitization, the rats are anaesthetized with sodium thiopental and fixed in the supine position. A polyethylene catheter was advanced into the trachea in a backward direction as far as the internal opening of the choanas for perfusion of the nasal cavity, so that it was possible for the solution to trickle out through the nasal cavities. A short tracheal catheter was tied into the trachea in an orthograde manner to make respiration possible. Phosphate-buffered saline solution (PBS) was continuously pumped for perfusion through the nasal cavity (0.5 ml/min) using a roller pump and collected by means of a fraction collector. Evans Blue was used as a plasma marker and injected intravenously (1 ml/animal each of a 1% strength solution in PBS) through a catheter in the jugular vein.

Substance administration was carried out topically. During administration, the test substance was added to the perfusion medium (PBS). The nasal mucous membrane was perfused for 30 min with PDE 4 inhibitor-containing solution. Evans Blue was then injected immediately before the start of the perfusion with ovalbumin-containing solution (challenge). After the start of the ovalbumin challenge (10 mg/ml of ovalbumin dissolved in PBS) 15 min fractions were collected every 15 min in the fraction collector over a period of 60 min. The Evans Blue concentration in the perfusates was measured with a Digiscan photometer at a wavelength of 620 nm. The blank values were automatically subtracted in the course of this. The course of action over 60 min was calculated using an AUC program. The substance action of the preparation group was calculated against vehicle controls in %.

$IC_{50}$ values in the range from $10^{-8}$ to $10^{-5}$ M were determined for the compounds of the present invention.

The utility of the compounds according to the invention of Formula (I) for the therapy of chronic obstructive pulmonary diseases is confirmed by the inhibition of LPS-induced TNFα release in human blood and by the inhibition of LPS-induced pulmonary neutrophil infiltration in ferrets and domestic pigs, all good animal models.

The stimulation of isolated leucocytes to cytokine release can take place in various ways. Lipopolysaccharides (LPSs) are a stimulus suitable for the investigation of TNFα release. LPS is a constituent of the bacterial cell walls and is released by killing the bacteria (antibiotics or immune system). LPS particularly stimulates the activity of the phagocytizing leucocytes (tissue macrophages, granulocytes, monocytes) and causes the infiltration of leucocytes from the blood stream into the affected tissue. A cytokine important for these mechanisms is TNFα, which is secreted in large amounts by the affected cells (the monocytes and macrophages are the main source) and initiates and maintains inflammation alongside other mediators.

For the investigation of the effect on LPS-induced TNFα release, human blood was obtained from various donors (inhibition of coagulation by means of citrate) and diluted 1:5 with RPMI 1640 cell culture medium. The test substances were added to the samples in various concentrations before the LPS challenge. The stimulation of the leucocytes was carried out 30 min later using lipopolysaccharides (LPS) from *Salmonella abortus equi* in a final concentration of 10 μg/ml. After incubation of the test batches for 24 hours at 37° C. and under 5% $CO_2$ in an incubator, the diluted blood was centrifuged and the TNFα concentration in the cell-free supernatant was measured by means of ELISA.

$IC_{50}$ values in the range from $10^{-7}$ to $10^{-5}$ M were determined for the compounds according to the invention.

An $IC_{50}$ value of 0.8 μmol/l, for example, was determined for the compound as in Example 1. In comparison with this, an $IC_{50}$ value of 7.0 μmol/l was determined with the reference standard SB 207499.

The inhibition of lipopolysaccharide (LSP)-induced pulmonary neutrophil infiltration by the substance is investigated in an in vivo test on male ferrets (0.6–2 kg). The experimental animals are anaesthetized with pentobarbital sodium (40 mg/kg of body weight i.p.), placed individually into a closed nebulization box of 5 capacity and exposed to an ultrasonically nebulized aerosol of 0.01% strength LPS (lipopolysaccharide) solution (additionally 0.1% hydroxylamine in PBS) for 10 minutes. The aerosol is generated by a nebulizer driven with compressed air (0.2 Mpa). Control animals are treated with an aerosol of physiological saline solution. The animals are observed during the entire process and removed from the nebulization box after admission of fresh air. On inhalation, nebulized LPS immediately induces inflammation of the airways, which is characterized by a massive infiltration of neutrophilic granulocytes into the lungs of the experimental animals. The neutrophilic achieves its maximum 4 to 6 hours after LPS exposure. In order to be able to measure the number of infiltrated neutrophilic granulocytes, the animals are anaesthetized with an overdose of ethylurethane (1.5 g/kg of body weight i.p.) 6 hours after LPS provocation and a bronchoalveolar lavage (BAL) is carried out using 2×10 ml of physiological saline solution. The number of cells in the pooled original BAL fluid (100 μl) are determined using the automatic cell-counting apparatus sold by Bayer Diagnostic under the trade designation Technicon H1E and the different leucocytes per μl are differentiated. In each test, 2 control groups (nebulization with physiological saline solution or with LPS solution) are included. Substances having anti-inflammatory activity, particularly those which affect TNFα release or the function of the neutrophilic granulocytes, inhibit the infiltration of leucocytes. The inhibition of infiltration is determined by the comparison of the number of infiltrated neutrophils in untreated experimental animals (with and without LPS provocation).

$ID_{50}$ values in the range from 1 to 20 mg/kg i.p. were determined for the compounds according to the invention. The compound of Example 1 was administered in doses of 1, 3 and 10 mg/kg i.p. 2 hours before LPS provocation to up to 3 experimental animals per dose. The neutrophilia in the BAL was inhibited in a dose-dependent manner (18%, 64% and 78%). The $ID_{50}$ is 2.4 mg/kg i.p. The administration of the selected PDE 4 inhibitor RPR-73401 (reference substance) caused an inhibition of neutrophilia of 49% in the dose 1 mg/kg i.p.

For intrapulmonary administration, the trachea of the animals is opened under anaesthesia with 40 mg/kg i.p. of pentobarbital sodium, 3% strength, 1.3 ml/kg, a 7 cm-long PVC catheter is tied in and the test substances are administered intrapulmonarily in powder form (mixed with lactose to 20 mg/kg) by means of a syringe 2 hours before LPS provocation. The intrapulmonary administration of Example 1 in doses of 1, 3 and 10 mg/kg inhibits LPS-induced neutrophilia in a dose-dependent manner (43%, 65% and 100%). The $ID_{50}$ is 1.65 mg/kg i.palm.

Pulmonary neutrophilia can be induced with LPS in domestic pigs in a manner similar to that in the ferret. The animals are anaesthetized with pentobarbital 10 mg/kg i.v., and intubated. Using a bronchoscope, a partial bronchoalveolar lavage is carried out in order to determine the proportion of neutrophilic granulocytes under physiological conditions. The test substance is then administered and the animals inhale an ultrasonically nebulized aerosol of 0.03% strength LPS (lipopolysaccharide) solution (additionally 0.1% hydroxylamine in PBS) through the tracheal tube for 20 min. The inhaled LPS induces a reactive inflammation of the airways and neutrophilic granulocytes infiltrate on a huge scale. The neutrophilia achieves its maximum 4 to 6 hours after LPS exposure. After 6 hours, the bronchoalveolar lavage is repeated and the increase in the neutrophil count is determined arithmetically.

Among animal species, the pig is particularly suitable for these investigations, since is has large anatomical and physiological similarities to man. For the compounds according to the invention, inhibitions of LPS-induced neutrophilia of 20% to 65% were determined on intrapulmonary administration of 10 mg/animal.

The intrapulmonary administration of the compound of Example 1 in the dose 10 mg/animal (about 0.75 mg/kg) inhibited LPS-induced pulmonary neutrophilia by 51%.

What is claimed is:

1. A process for preparing a compound of formula 1

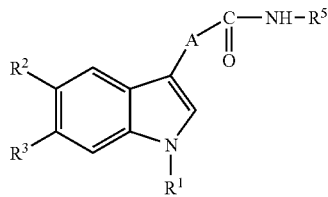

or a salt thereof, wherein
$R^1$ is a straight or branched $C_{1-12}$ alkyl optionally substituted with phenyl, or $C_{3-8}$ cycloalkyl radical wherein the phenyl radical is optionally substituted with a halo, nitro, hydroxy, $C_{1-4}$ alkyl, $C_{1-4}$ alkoxy, or COOH;
$R^2$ and $R^3$ are each independently of each other hydrogen or an OH radical where at least one of $R^2$ and $R^3$ are —OH;
$R^5$ is a or pyridyl radical substituted with at least one halogen radical and is optionally further substituted with —H, —OH, —SH, —NH$_2$, —NHC$_{1-6}$ alkyl, —N(C$_{1-6}$ alkyl)$_2$, —NHC$_{6-14}$ aryl, —N(C$_{6-14}$ aryl)$_2$, —N(C$_{1-6}$ alkyl)(C$_{6-14}$ aryl), —NHCOR$^6$, —NO$_2$, —CN, —COOH, —(CO)R$^6$, —(CS)R$^6$, —F, —Cl, —Br, —I, —O—C$_{1-6}$ alkyl, —O—C$_{6-14}$ aryl, —O(CO)R$^6$, —S—C$_{1-6}$ alkyl, —S—C$_{6-14}$, aryl, —SOR$^6$, or —SO$_2$R$^6$—; and
A is a bond, C=O, or a CHOH radical or a pharmaceutically acceptable salt thereof, which method comprises converting a compound of formula (I), wherein $R^2$ or $R^3$ or $R^2$ and $R^3$ are O—$R^7$, into the compound of formula (I) by removing $R^7$, wherein $R^7$ is a substituent that is a protecting group selected from the group consisting of alkyl and aralkyl Lewis acid to cleave the ether and remove $R^7$, to yield the compound of formula (I), wherein said compound of formula (I) is selected from the group consisting of N-(3,5-dichloropyridin-4-yl)-2-(1-(4-fluorobenzyl)-5-hydroxyindol-3-yl)-2-hydroxyacetamide, N-(3,5-dichloropyridin-4-yl)-2-(1-(2,6-difluorobenzyl)-5-hydroxyindol-3-yl)-2-oxoacetamide, N-(3,5-dichloropyridin-4-yl)-2-(1-(3-nitrobenzyl)-5-hydroxyindol-3-yl)-2-oxoacetamide, N-(3,5-dichoropyridin-4-yl)-2-(1-propyl-5-hydroxyindol-3-yl)-2-oxoacetamide, N-(3,5-dichloropyridin-4-yl)-2-(1-isopropyl-5-hydroxyindol-3-yl)-2-oxoacetamide, N-(3,5-dichoropyridin-4-yl)-2-(1-cyclopentylmethyl-5-hydroxyindol-3-yl)-2-oxoacetamide, N-(3,5-dichloropyridin-4-yl)-2-(1-(4-fluorobenzyl)-6-hydroxyindol-3-yl)-2-oxoacetamide, N-(3,5-dichlopyridin-4-yl)-5-hydroxy-1-(4-methoxybenzyl)indole-3-carboxamide and N-(3,5-dichloropyridin-4-yl)-2-(1-(4-fluorobenzyl)-5-hydroxyindol-3-yl)-2-oxoacetamide.

2. The method of claim 1, wherein $R^5$ is substituted with one or two halogens.

3. The method of claim 1, wherein $R^1$ is an optionally substituted $C_1$–$C_2$ alkyl.

4. The method of claim 3, wherein $R^1$ is an optionally substituted $C_1$–$C_2$ alkyl.

5. The method of claim 1, wherein $R^7$ is methyl or ethyl.

6. The method of claim 5, wherein $R^7$ is methyl.

7. The method of claim 1, wherein the Lewis acid is selected from the group consisting of BBr$_3$ and AlCl$_3$.

8. The method of claim 7, wherein said Lewis acid is BBr$_3$.

9. The method of claim 7, wherein removal of $R^7$ is in the presence of an additional activator.

10. The method of claim 9, wherein the additional activator is selected from the group consisting of ethane-1,2-dithiol and benzyl mercaptan.

11. The method of claim 7, wherein said Lewis acid is AlCl$_3$.

12. The method of claim 1, wherein the ether cleavage is conducted at elevated or normal pressure.

13. The method of claim 1, wherein the ether cleavage takes place in the presence of a suitable catalyst.

14. A method for producing N-(3,5-dichloropyridin-4-yl)-2-(1-(4-fluorobenzyl)-5-hydroxyifldol-3-yl)-2-oxoacetamide by reacting a solution of N-(3,5-dichloropyridin-4-yl)-2-(1-(4-fluorobenzyl)-5-methoxyindol-3-yl)-2-oxoacetamide with BBr$_3$ while heating to form a heated solution, cooling the heated solution to yield a cooled solution, and mixing the cooled solution with an aqueous sodium hydrogencarbonate solution to crystallize the N-(3,5-dichloropyridin-4-yl)-2-(4-fluorobenzyl)-5-hydroxyindol-3-yl)-2-oxoacetamide.

15. The method of claim 1, wherein the compound is N-(3,5-dichloropyridin -4-yl)-2-(1-(4-fluorobenzyl)-5-hydroxyindol-3-yl)-2-oxoacetamide sodium salt.

16. The method of claim 14, wherein the solution is stirred during heating.

17. The method of claim 16, wherein the solution is stirred during cooling.

18. The method of claim 14, further comprising recovering the crystallized N-(3,5-dichloropyridin-4-yl)-2-(1-(4-fluorobenzyl)-5-bydroxyiridol-3-yl)-2-oxoacetamide.

19. The method of claim 17, further comprising recovering the crystallized N-(3,5-dichloropyridin-4-yl)-2-(4-fluorobenzyl)-5-hydroxyindol-3-yl)-2-oxoacetamide.

20. The method of claim 19, wherein the solution is cooled to 20° C.

21. The method of claim 14, further comprising recrystallizing the crystallized N-(3,5-dichloropyridin-4-yl)-2-(1-(4-fluorobenzyl)-5-hydroxyindol-3-yl)-2-oxoacetamide.

22. The method of claim 1, wherein the compound is a pharmaceutically acceptable salt of the compound.

23. The method of claim 1, wherein the compound is N-(35-dichloropyridin -4-yl)-2-(1(4-fluorobenzyl)-5-hydroxyindol-3-yl)-2-hydroxyacetamide.

24. The method of claim 1, wherein the compound is N-(3,5-dichloropyridin -4-yl)-2-(-(2,6-difluorobenzyl)-5-hydroxyindol-3-yl)-2-oxoacetamide.

25. The method of claim 1, wherein the compound is N-(3,5-dichloropyridin -4-yl)-2-(1-(3-nitrobenzyl)-5-hydroxyindol-3-yl)-2-oxoacetamide.

26. The method of claim 1, wherein the compound is N-(3,5-dichloropyridin -4-yl)-2-(1-propyl-5-hydroxyindol-3-yl)-2-oxoacetamide.

27. The method of claim 1, wherein the compound is N-(3,5-dichloropyridin -4-yl)-2-(1-isopropyl-5-hydroxyindol-3-yl)-2-oxoacetamide.

28. The method of claim 1, wherein the compound is N-(3,5-dichloropyridin -4-yl)-2-(1-cyclopentylmethyl-5-hydroxyindol-3-yl)-2-oxoacetamide.

29. The method of claim 1, wherein the compound is N-(3,5-dichloropyridin -4-yl)-2-(1-(4-fluorobenzyl)-6-hydroxyindol-3-yl)-2-oxoacetamide.

30. The method of claim 1, wherein the compound is N-(3,5-dichloropyridin -4-yl)-5-hydroxy-1-(4-methoxybenzyl)indole-3-carboxamide.

\* \* \* \* \*